US010297140B2

(12) United States Patent
Cavalcanti et al.

(10) Patent No.: US 10,297,140 B2
(45) Date of Patent: May 21, 2019

(54) EMERGENCY RESPONSE AND TRACKING USING LIGHTING NETWORKS

(71) Applicant: SIGNIFY HOLDING B.V., Eindhoven (NL)

(72) Inventors: Dave Alberto Tavares Cavalcanti, Mahopac, NY (US); Amjad Soomro, Hopewell Junction, NY (US); Jianfeng Wang, Ossining, NY (US)

(73) Assignee: SIGNIFY HOLDING B.V., Eindhoven (NL)

( * ) Notice: Subject to any disclaimer, the term of this patent is extended or adjusted under 35 U.S.C. 154(b) by 489 days.

(21) Appl. No.: 14/370,132

(22) PCT Filed: Jan. 2, 2013

(86) PCT No.: PCT/IB2013/050023
§ 371 (c)(1),
(2) Date: Jul. 1, 2014

(87) PCT Pub. No.: WO2013/102855
PCT Pub. Date: Jul. 11, 2013

(65) Prior Publication Data
US 2015/0002292 A1 Jan. 1, 2015

Related U.S. Application Data

(60) Provisional application No. 61/583,636, filed on Jan. 6, 2012.

(51) Int. Cl.
*G08B 1/08* (2006.01)
*G08B 25/01* (2006.01)
(Continued)

(52) U.S. Cl.
CPC .............. *G08B 25/016* (2013.01); *G01S 1/70* (2013.01); *G06F 19/3418* (2013.01);
(Continued)

(58) Field of Classification Search
CPC .. G08B 25/016; G08B 21/02; G08B 21/0211; G08B 21/0258; G08B 21/0272;
(Continued)

(56) References Cited

U.S. PATENT DOCUMENTS 5,228,449 A * 7/1993 Christ ................ A61B 5/02433
600/504
6,014,080 A * 1/2000 Layson, Jr. ........ G08B 21/0211
340/539.1
(Continued)

FOREIGN PATENT DOCUMENTS

JP 2002261955 A 9/2002
JP 2009206620 A 9/2009
(Continued)

OTHER PUBLICATIONS

Barnes, Richard "Internet Geolocation and Location-based Services", IEEE Communications Magazine, Apr. 2011.

Primary Examiner — Quang Pham

(57) ABSTRACT

Obtaining a target location of a user associated with a body worn device (50) that receiving information related to a condition of user and communicates an indication of the condition to a server (12) over a network (24). The method including: providing a network (24) formed of a plurality of lighting units (42, 32) and a database (22) for maintaining information describing a geographic location of each of the plurality of lighting units, each lighting unit transmitting a unique identifier; providing the body worn device with a lighting unit identifier sensor (52), the sensor receiving lighting unit identifiers of at least one of the plurality of lighting units; the body worn device communicating the received lighting unit identifiers with the indication in a message to the server via the network; and the database providing a geographic location of the one or more lighting (Continued)

Figure 1:
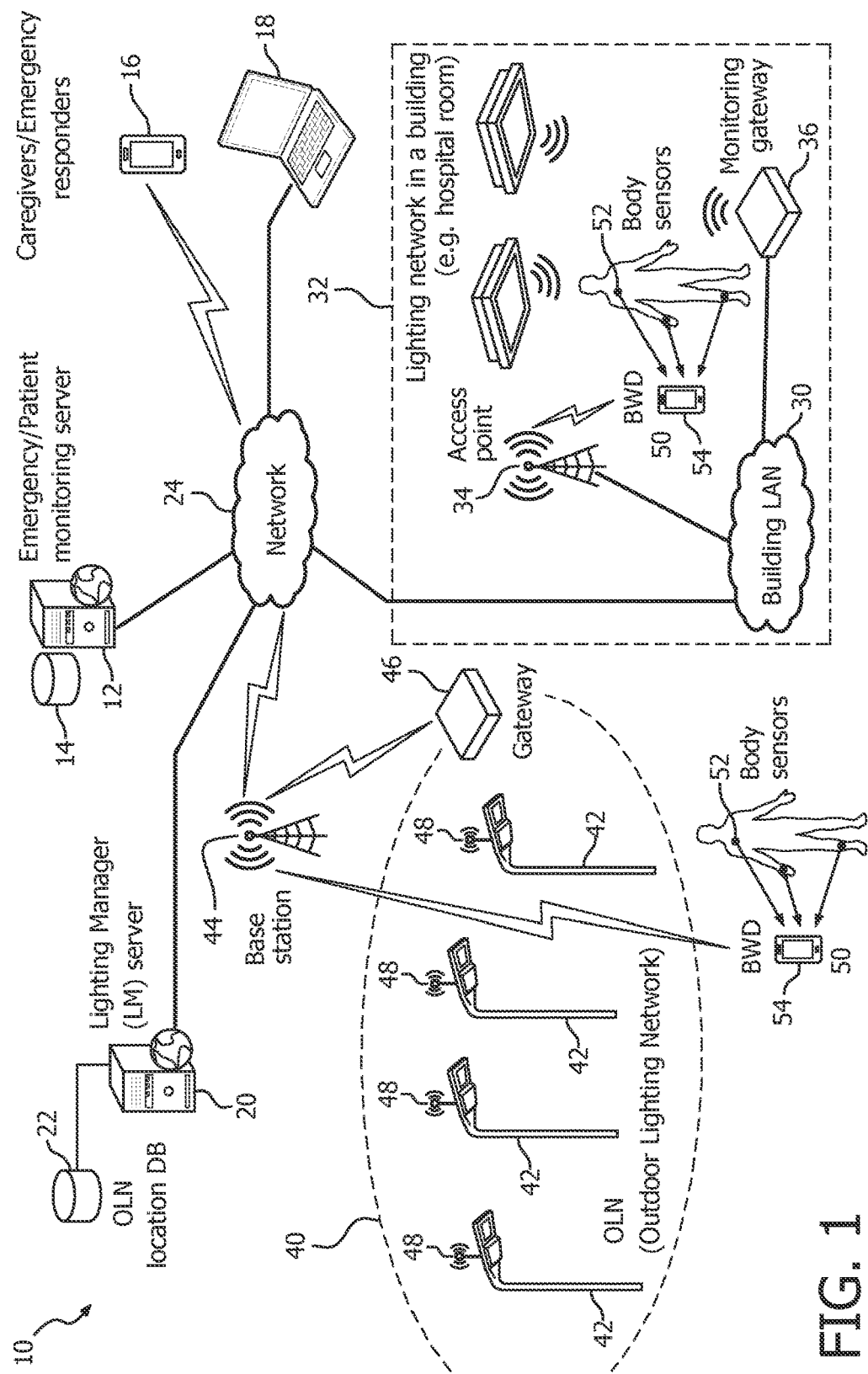

units, the geographic location corresponding to the target location of the body worn device.

18 Claims, 3 Drawing Sheets

(51) Int. Cl.
| | |
|---|---|
| *G08B 21/02* | (2006.01) |
| *G08B 21/04* | (2006.01) |
| *G07C 9/00* | (2006.01) |
| *G06F 19/00* | (2018.01) |
| *G01S 1/70* | (2006.01) |

(52) U.S. Cl.
CPC .......... *G07C 9/00111* (2013.01); *G08B 21/02* (2013.01); *G08B 21/0211* (2013.01); *G08B 21/0258* (2013.01); *G08B 21/0272* (2013.01); *G08B 21/0275* (2013.01); *G08B 21/0453* (2013.01); *G08B 21/0461* (2013.01); *G08B 21/0476* (2013.01)

(58) Field of Classification Search
CPC ............ G08B 21/0275; G08B 21/0453; G08B 21/0461; G08B 21/0476; G01S 1/70; G06F 19/3418; G07C 9/00111
See application file for complete search history.

(56) References Cited

U.S. PATENT DOCUMENTS

| | | | | |
|---|---|---|---|---|
| 6,626,837 B2* | 9/2003 | Muramatsu | ........ | A61B 5/02438 600/459 |
| 7,480,501 B2 | 1/2009 | Petite | | |
| 8,428,469 B2* | 4/2013 | Kim | .................... | H04W 72/048 398/127 |
| 8,510,033 B2* | 8/2013 | Park | ....................... | G01C 21/20 398/43 |
| 8,902,076 B2* | 12/2014 | Pederson | ........... | G07C 9/00158 340/815.45 |
| 8,979,765 B2* | 3/2015 | Banet | .................... | A61B 5/0809 600/484 |
| 9,509,402 B2* | 11/2016 | Ryan | .................... | H04B 10/116 |
| 2004/0141173 A1* | 7/2004 | Rekimoto | ............... | G01C 15/00 356/141.5 |
| 2005/0035862 A1* | 2/2005 | Wildman | ............... | A61B 5/1113 340/573.1 |
| 2006/0033623 A1 | 2/2006 | Hines | | |
| 2006/0071798 A1 | 4/2006 | Kiff | | |
| 2006/0158534 A1* | 7/2006 | Gotohda | ................ | H04N 5/232 348/239 |
| 2006/0281979 A1 | 12/2006 | Kim et al. | | |
| 2007/0132576 A1 | 6/2007 | Kolavennu | | |
| 2007/0139199 A1 | 6/2007 | Hanlon | | |
| 2007/0270666 A1* | 11/2007 | Amano | ................ | A61B 5/0059 600/300 |
| 2008/0021731 A1* | 1/2008 | Rodgers | ................ | A61B 5/1113 705/2 |
| 2008/0076450 A1* | 3/2008 | Nanda | .................... | G01D 21/00 455/456.1 |
| 2008/0122696 A1 | 5/2008 | Huseth | | |
| 2008/0248813 A1* | 10/2008 | Chatterjee | ................. | G01S 1/68 455/456.2 |
| 2009/0033500 A1* | 2/2009 | Malik | .................... | A62B 99/00 340/572.8 |
| 2009/0088605 A1* | 4/2009 | Ross | .................... | A61B 5/0002 600/300 |
| 2009/0138336 A1* | 5/2009 | Ashley, Jr. | ............ | G01S 5/0289 455/456.1 |
| 2009/0138353 A1* | 5/2009 | Mendelson | .......... | G01C 21/206 705/14.39 |
| 2009/0143045 A1* | 6/2009 | Graves | ................ | A61B 5/02055 455/404.1 |
| 2009/0231125 A1* | 9/2009 | Baldus | .................. | A61B 5/0006 340/539.12 |
| 2009/0273455 A1* | 11/2009 | Sweeney | ................ | A61B 5/1113 340/286.07 |
| 2010/0138379 A1* | 6/2010 | Mott | ..................... | A61B 5/4857 706/52 |
| 2010/0164712 A1* | 7/2010 | Corrigan | ............ | G08B 13/1481 340/539.13 |
| 2010/0298655 A1* | 11/2010 | McCombie | .......... | A61B 5/0002 600/301 |
| 2011/0125535 A1* | 5/2011 | Gross | ...................... | G16H 10/65 705/3 |
| 2011/0128824 A1* | 6/2011 | Downey | ............ | A63B 24/0021 368/14 |
| 2011/0152702 A1* | 6/2011 | Goto | ...................... | A61B 5/0006 600/508 |
| 2011/0221688 A1* | 9/2011 | Byun | ...................... | H04B 1/385 345/173 |
| 2012/0050532 A1* | 3/2012 | Rhyins | ...................... | G01S 5/14 348/143 |
| 2012/0169467 A1* | 7/2012 | Condra | ............... | G06F 19/3418 340/8.1 |
| 2012/0218115 A1* | 8/2012 | Chupa | ...................... | G08B 21/22 340/686.6 |
| 2012/0221254 A1* | 8/2012 | Kateraas | ........... | A61B 5/02055 702/19 |
| 2012/0238800 A1* | 9/2012 | Naujokat | .............. | A61B 5/0402 600/26 |
| 2012/0268269 A1* | 10/2012 | Doyle | ................ | G08B 21/0202 340/539.13 |
| 2012/0274508 A1* | 11/2012 | Brown | .................... | G04F 10/00 342/357.25 |
| 2012/0306621 A1* | 12/2012 | Muthu | ............... | H05B 37/0272 340/8.1 |
| 2013/0030825 A1* | 1/2013 | Bagwandeen | ........ | G06F 19/327 705/2 |
| 2013/0109997 A1* | 5/2013 | Linke | .................. | G06F 19/3418 600/549 |
| 2013/0148020 A1* | 6/2013 | Cook | .................. | H05B 37/0272 348/460 |
| 2013/0237778 A1* | 9/2013 | Rouquette | .......... | A61B 5/02438 600/301 |
| 2013/0300578 A1* | 11/2013 | Uchida | ................ | A61B 5/0022 340/870.02 |
| 2013/0324865 A1* | 12/2013 | Yavelov | ................ | A61B 5/681 600/494 |
| 2014/0235269 A1* | 8/2014 | Ericsson | ............ | H05B 37/0272 455/456.1 |
| 2014/0308048 A1* | 10/2014 | Roberts | .................... | H04L 27/10 398/187 |

FOREIGN PATENT DOCUMENTS

| | | |
|---|---|---|
| JP | 2010107235 A | 5/2010 |
| JP | 2010146447 A | 7/2010 |
| WO | 2008045436 A2 | 4/2008 |
| WO | 2013064979 A1 | 5/2013 |

* cited by examiner

EMERGENCY RESPONSE AND TRACKING USING LIGHTING NETWORKS

CROSS-REFERENCE TO PRIOR APPLICATIONS

This application is the U.S. National Phase application under 35 U.S.C. § 371 of International Application No. PCT/IB2013/050023, filed on Jan. 2, 2013, which claims the benefit of U.S. Provisional Patent Application No. 61/583, 636, filed on Jan. 6, 2012. These applications are hereby incorporated by reference herein.

This invention is directed to user monitoring and tracking for example by healthcare and emergency response services and more specifically to user localization and tracking using indoor and outdoor lighting networks.

As user health monitoring is becoming ubiquitous, alerts or alarms indicating a users need for immediate assistance may be generated anytime, anywhere either indoors or outdoors. For instance, body worn devices used for health monitoring applications can generate alarms or alerts that are communicated to caregivers at remote locations or at central monitoring and remote response stations. The alerts or alarms indicating criticality of the users condition may require immediate assistance from the caregivers; thus tracking the precise location of the user wearing the device, e.g., which building, which wing or section of the building, which floor, room, etc., becomes critical.

Typically, alarms or alerts are triggered by the devices or by a central monitoring or remote response stations. Once a critical alarm or alert is generated, identifying the precise location of the user wearing the device, e.g., in a hospital, a building or outdoors on a street, is needed in order for the caregivers and emergency responders to provide timely assistance. In addition to pinpointing the location of the users wearing the devices in an emergency, it is also desirable to track whereabouts of that user at least for a certain interval before the alarm was triggered. Such tracking information may provide insights into the condition of the user.

A variety of wireless communication networks may be used to connect the devices to the central monitoring and remote response stations, including cellular networks, Internet based networks, e.g., WiFi, or dedicated/proprietary networks, e.g., Wireless Medical Telemetry Systems, etc. These wireless technologies may also provide localization services, however with different levels of precision. A survey of localization technologies can be found in R. Barnes, et al, Internet Geolocation and Location-based Services, IEEE Communications Magazine, April 2011, the contents of which is incorporated herein by reference thereto.

GPS-based localization is very precise when a view of the sky is unobstructed but do not work well inside buildings. The cellular networks and WiFi positioning using cell IDs and measurements may provide precise localization when the device is within coverage of several base stations or access points. However, ambiguities generated by the surrounding environment, e.g. building infrastructure, may impact the tracking performance. For instance, in a hospital, or some building with dense population, precision of a few meters may generate ambiguities in terms of rooms, floors, or hospital beds required to uniquely identify the user, such as a patient in the hospital. Furthermore, localization techniques can significantly increase power consumption of the devices which are predominantly battery powered and must use energy in a very conservative manner. Therefore, tracking the location of a device for a relative long time with existing localization techniques may not be practical given the typical battery capacity and required charge times.

It is also noted that a typical central health monitoring system does not have information about city, street, or building layout and instead rely on external systems for the location service. Coordination and communication between the health systems and such external systems for device tracking and localization is not well defined in the existing art.

Thus, what is needed is user localization and tracking for healthcare and emergency response systems that solves the power and localization problems found in prior systems.

It is an object of the present system to overcome disadvantages and/or make improvements in the prior art.

It is another object of the present system to precisely indicate a location of a person using a body worn device.

Accordingly, described is a system, method and device for obtaining a target location of a user associated with a body worn device that through the use of sensor information detects a condition of the user including health conditions and communicate an indication regarding the detected condition to a server over a network. The method includes providing a network formed of a plurality of lighting units and a database for maintaining information describing a geographic location of each of the plurality of lighting units, each lighting unit transmitting a unique identifier; providing the one or more body worn devices with a lighting unit identifier sensor, the sensor receiving lighting unit identifiers of at least one of the plurality of lighting units; the one or more body worn devices communicating the received lighting unit identifiers with the indication to a server via the network; and the database providing a geographic location of the one or more lighting units, the geographic location corresponding to the target location of the body worn device.

The unique identifier may be transmitted using electromagnetic radiation, such as one of modulated light in invisible or visible spectrum. The lighting unit identifier sensor may be selected from being integrated with the body worn device and being placed on or around the body worn device to enhance detection performance. The lighting unit identifier sensor may be wirelessly connected to the one or more body worn devices. The body worn device may communicate when the indication is generated, periodically, at predetermined times, and/or when certain predetermined conditions are met.

The communication may further include timestamps associated with one or more lighting unit identifiers for indicating the time a particular lighting unit identifier was received. The body worn device may include a memory for storing the lighting unit identifiers and associated timestamps indicating when the individual lighting unit identifiers were received. The communicated one or more lighting unit identifiers may include many lighting unit identifiers having different time stamps for obtaining a plurality of target locations and may form a trajectory of the body worn device over time. The trajectory may be used to assess a health condition of the user with the body worn device.

Further, when a single lighting unit identifier is provided in the message the location of the lighting unit is the target location which is an approximation of the location of the user, and when a plurality of lighting unit identifiers is provided in the message with temporally close timestamps the locations of the plurality of lighting units may be used to determine the target location. The method may further include requesting the database to provide geographic location of the one or more lighting units and alerting at least one emergency responder that a user wearing the body worn device requires assistance at the target location. The target location may be identified with at least one of building section, floor number and room number; zip code, street name, and house number; a building or city map with target location identified; latitude, longitude and altitude; a relative position with respect to a predetermined location; and relative position with respect to another location conveyed in the query response.

Figure 2:
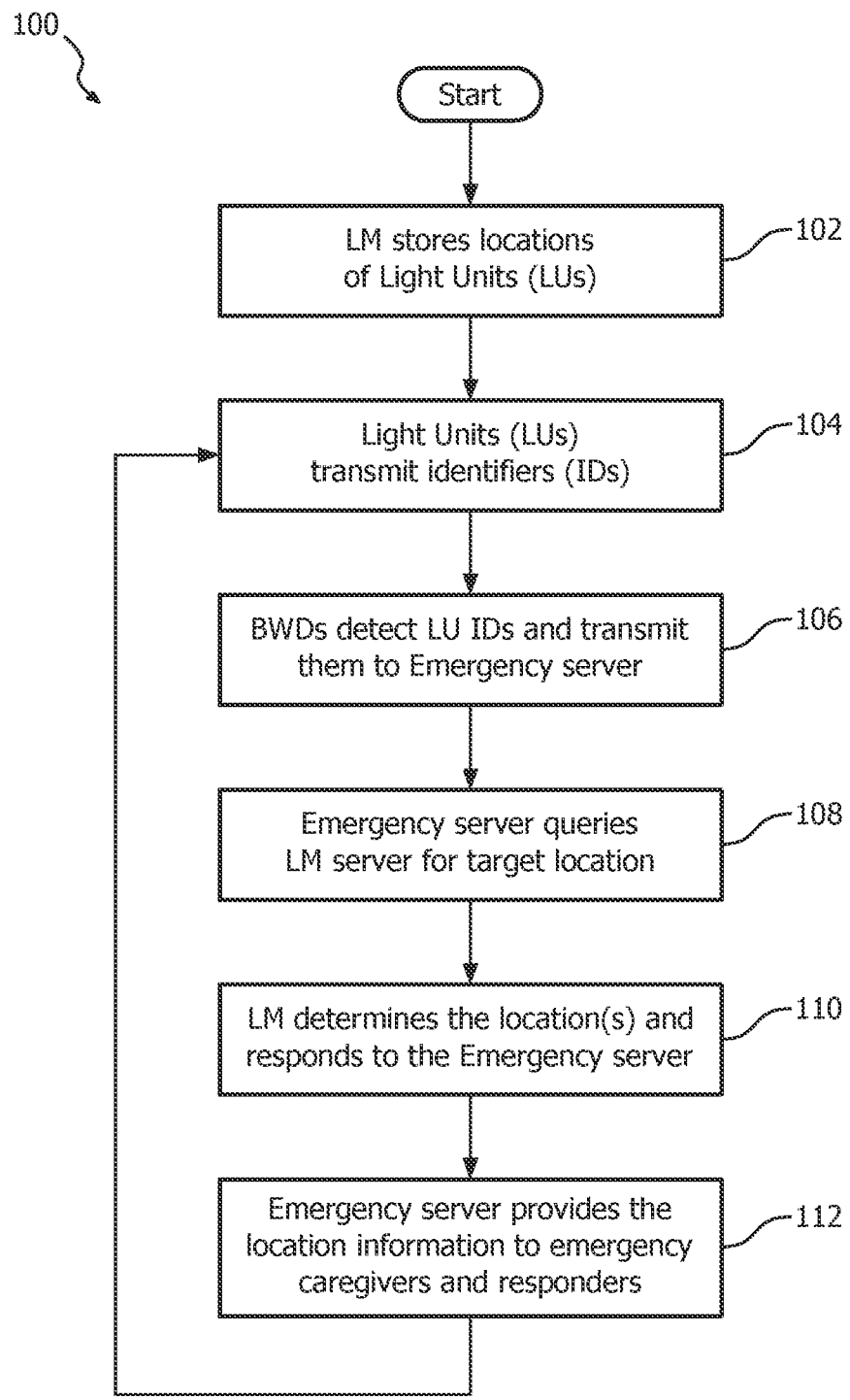
Figure 3:
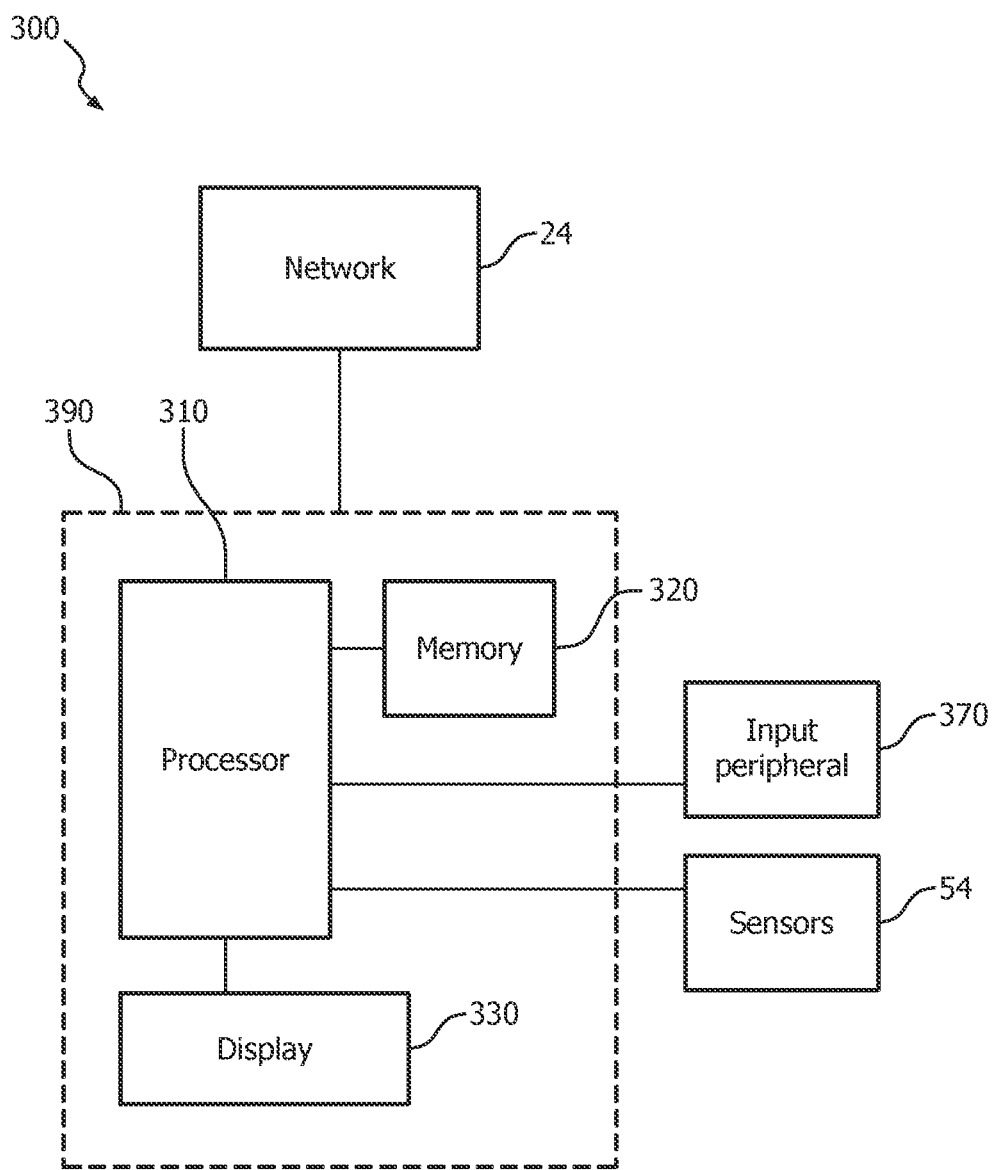

The present system is explained in further detail, and by way of example, with reference to the accompanying drawings wherein:

FIG. 1 is a diagram illustrating architecture and components in accordance with embodiments of the present system; and FIG. 2 is a flowchart describing the general tracking process involving the lighting network, the devices and an emergency monitoring server in accordance with embodiments of the present system; and FIG. 3 shows a portion of a system in accordance with embodiments of the present system.

The following are descriptions of illustrative embodiments that when taken in conjunction with the following drawings will demonstrate the above noted features and advantages, as well as further ones. In the following description, for purposes of explanation rather than limitation, illustrative details are set forth such as architecture, interfaces, techniques, element attributes, etc. However, it will be apparent to those of ordinary skill in the art that other embodiments that depart from these details would still be understood to be within the scope of the appended claims. Moreover, for the purpose of clarity, detailed descriptions of well known devices, circuits, tools, techniques and methods are omitted so as not to obscure the description of the present system. It should be expressly understood that the drawings are included for illustrative purposes and do not represent the scope of the present system. In the accompanying drawings, like reference numbers in different drawings may designate similar elements.

FIG. 1 shows a diagram illustrating architecture and components in accordance with embodiments of the present system. The present system is based on a realization that lighting systems like that described in a co-pending patent application titled: "Enhanced Lighting Network to Serve Mobile Cellular Users and Method of Operation thereof" (U.S. Patent Application No. 61/553,436, filed Oct. 31, 2011), the complete contents of which are incorporated herein by reference, may be used to used to benefit tracking of one or more body wearable devices so as to pinpoint the location of its user when desired. These lighting systems have begun to incorporate wired or wireless communication features through a backhaul infrastructure to enable communication with networks for lighting management. The backhaul infrastructure of the lighting system includes links between a main communication network such as the Internet, to local lighting systems such as through a gateway. These links may be between lighting unit(s) and the gateway itself and/or may be between lighting units, such as for relayed communications between lighting units for reaching a gateway for communicating with a backend management system. Accordingly, these lighting systems may access networks through the backhaul infrastructure using couplings such as the Internet via wired or wireless communication methods such as fiber, powerline, Ethernet, WiFi, cable, very high-speed DSL (VDSL), RF mesh, cellular, visible light communication (VLC), etc., for lighting management purposes such as to control lighting units (e.g., turn on/off, dim, etc.) throughout the lighting system.

As illustrated in FIG. 1, lighting units 42, 32 and backhaul infrastructure including communication technologies such gateways 46, 36, access points 34 and base stations 44 may be combined together in lighting networks 40, 30. In accordance with embodiments of the present system, individual lighting units 42, 32 may include IDs that uniquely identify each lighting unit 42, 32 enabling easy discovery of information relevant to each lighting unit. The information may be stored in a database 22 and may include the lighting unit's energy efficiency, inventory inspection, control, type, age, maintenance record, etc., and pertinently a physical and/or geographic location of the lighting units 42, 32. The database 22 may be managed by a lighting manager server 20 and may further include information related to management of lighting networks 40, 30. Further, the database 22 may include a locations map for identifying a geographic location of the lighting units 42, 32. Given lighting units 42, 32 IDs, the lighting management server 20 may determine geographic locations of one or more of the lighting units 42, 32 such as by using the lighting unit ID to query the database 22 for the lighting unit geographic location. Furthermore, in cases where multiple lighting unit IDs are received such as in a timed order, the lighting management server 20 may determine the geographic location by combining the location of the multiple lighting units 42, 32, e.g., using triangulation.

In accordance with embodiments of the present system, the lighting units 42, 32 may be equipped with transceivers 48 (e.g., transmitters/receivers), which are enabled to communicate, e.g., wirelessly and/or through a wire, with the lighting manager server 20 for example through the gateway 46 and the network 24, such as by sending status messages. As may be readily appreciated, one or more of the gateways shown may be connected directly to the network, for example without going through a base station, such as though a wired connection, etc. Further, other connections between the lighting units and the lighting manager server are possible. In accordance with embodiments of the present system, the lighting units may alternatively or in addition connect directly to the BS without a gateway. Further, the lighting units may communicate with other lighting units to reach one or more of the lighting manager 20 and/or an emergency monitoring server 12 as described herein.

In accordance with embodiments of the present system, such status messages may be periodic beacon messages sent at some predetermined interval for example indicating whether everything is working properly or not, indicating current lighting conditions, indicating current atmospheric conditions, etc. The status messages may be sent to the lighting manager server 20 such as though the gateway 46, 36 directly from the lighting unit sending the status message and/or may be relayed though another lighting unit. In accordance with embodiments of the present system, the gateway 46, 36 may relay the status messages to the lighting manager server 20 for example via the base station 44, 34 and a network 24, such as the Internet or some other wide area network, e.g., a telephone and/or cellular networks.

In accordance with embodiments of the present system, the lighting units 42, 32 may emit the device ID locally (e.g., in proximity to the lighting units) in a form that is detectable by a body worn device 50 (BWD) in proximity to the lighting unit. For example, the lighting units 42, 32 may emit electromagnetic radiation for example that is not visible and may be modulated/coded to include an indication of the device ID. Such emitted electromagnetic radiation may be used outdoors and/or indoors for example when the lighting units 42, 32 are ON at night and when they are OFF during day time when in general illumination light is turned off. In accordance with embodiments of the present system, the lighting units 42, 32 may transmit an indication of the device ID through other systems, such as through operation of a radio frequency identification (RFID) system, etc. In accordance with embodiments of the present system, other communication protocols may include 802.15.4, ZigBee, 802.11 including other proprietary implementations of one or more of these protocols.

For the discussed embodiments and variations thereof, the lighting units 42, 32, which are ubiquitous in indoor and most outdoor environments generating general illumination light, are amenable to providing a cost-effective localization and/or tracking solution and to addressing specific needs arising in user monitoring including health monitoring and emergency response applications. In accordance with embodiments of the present system, the lighting manager server 20 using the information stored in the database 22 may utilize the unique identity of each lighting unit 42, 32 to identify corresponding geographic locations of the lighting units 42, 32.

In accordance with embodiments of the present system, body worn devices 50 may be used for health monitoring applications and may include sensors 52 such as body sensors for determining alarm conditions for example when these sensors 52 detect abnormal readings from a corresponding user. To facilitate the following discussion, the term body worn device will be utilized herein to indicate a device that is carried by a user such that determining a location of the body worn device is used for determining a location of the user. In accordance with embodiments of the present system, the body worm device may be a dedicated monitoring device such as a health monitoring device and/or may be a multipurpose device, such as a smart phone wherein user monitoring through use of one or more sensors is only one of many operations of the device.

In accordance with embodiments of the present system, one or more of the sensors may be positioned within the environment of the user as opposed to being physically worn on the body. For example, in accordance with embodiments of the present system, one or more of the sensors may be positioned around a living area such as on/within a floor as one or more pressure sensors on/within the floor that for example may detect user activity such as user trajectory, a user fall during user monitoring, etc., for purposes of generating an alarm as described herein. One or more of the sensors may include a camera sensor for example attached to a light pole. As may be readily appreciated, many different types of sensors may provide information that may be utilized for determining a condition of the user, such as an alarm condition and are intended to be encompassed by the present system. One or more of the sensors including the sensors in the environment may communicate with the body worn device for purposes of determining a condition of the user and notifying a health management server accordingly. In accordance with embodiments of the present system, the sensor information may be utilized by the body worn device for purposes of determining a condition of the user and/or may be forwarded to the health management server for determining the condition of the user.

The devices 50 may include associated sensors 54 that are enabled to sense wireless communication and/or electromagnetic radiation transmissions, for example, emanating from the lighting units 42, 32 and decode the device IDs from the messages and/or the modulated/coded electromagnetic radiation, such as light. Hereinafter the term "light sensor" is utilized to distinguish the operation of detecting the device IDs from the operation of detecting a condition of the user, however, in accordance with embodiments of the present system, a same sensor (e.g., camera) may be utilized for sensing the device IDs as well as for sensing a condition of the user. The light sensor 54 may be physically integrated within the device 50 and/or may be flexibly placed on or around the body to enhance reception performance. In embodiments of the present system where the light sensor 54 is separate from the device 50, the light sensor 54 may communicate with the device 50 through wired and/or wireless links. Such wireless links may be based on, for example, wireless medical body area network, Bluetooth, Zigbee, etc.

When present, the light sensors 54 may detect transmissions from many lighting units 42, 32 at a given geographic location, where the transmissions may include the same or temporally close timestamps and corresponding lighting unit IDs at a given geographic location. The information from such transmissions, e.g., the lighting units IDs and associated timestamps indicating when transmissions from the respective lighting units 42, 32 were received, may be stored in the devices memory (e.g., see, FIG. 3, memory 320).

As described, the devices 50 monitor one or more of the sensors 52 and upon detection of an abnormality or a predetermined condition of the user, the devices may generate a notification message for the health management server such as an alarm. Further, the devices 50 through for example operation of the light sensor 54 may detect (e.g., sense) the device IDs of nearby lighting units 42, 32 (e.g., at the same time, simultaneously and/or immediately preceding the detection of a condition of the user and/or a generation of an alarm). Consequently, in response to the detection of a condition of the user, such as an alarm condition, the device 50 may forward through use of a transceiver of the device the generated alarm and the sensed device IDs to an emergency monitoring server 12 having a database 14. In accordance with embodiments of the present system, the device 50 may utilize a communication network, such as a cellular communication network to communicate with the emergency monitoring server 12. Further, the device 50 may utilize the backhaul infrastructure of the lighting network 40 to communicate with the emergency monitoring server 12.

In accordance with embodiments of the present system, this communication indicates to the emergency monitoring server 12 that a user of the body wearable device 50 has for example encountered a health problem in the vicinity of the detected nearby lighting units 42, 32 and assistance might be necessary. As may be readily appreciated, in accordance with embodiments of the present system, the detected condition may be simply that there are no detected abnormalities of the user. For example, the system may support a query system where a users condition may be assessed to determine whether or not abnormalities are detected. As discussed above, the IDs through use of the database 22 may be utilized to determine the geographic location of the lighting units 42, 32 and, therefore, the location of the corresponding device 50 and the corresponding user.

In accordance with embodiments of the present system, to determine the geographic location, the emergency monitoring server 12 may send, via the network 24, the sensed IDs to the lighting management server 20 for determination of the geographic location of the lighting units 42, 32 corresponding to the sensed IDs. In operation, the lighting management server 20 may utilize the sensed IDs for querying the database 22 to determine the geographic location of the lighting units 42, 32 and thereby the geographic location of the corresponding user which may thereafter be returned to the emergency monitoring server 12. As may be readily appreciated, the emergency monitoring server 12 may maintain the database 22 and/or may simply be provided the database 22 prior to receipt of sensed IDs. In these embodiments, there is no need for the emergency monitoring server 12 to interact with the lighting management server 20 at the time of receiving sensed IDs since it already has the database for determining the geographic location of the lighting units 42, 32 and thereby the geographic location of the corresponding user.

In either event, the emergency monitoring server 12 may then determine, based on information in its database 14 what actions to take and which caregivers 16 and emergency responders 18 to alert. As is apparent to these skilled in the art, the network 24 used between the devices 20 and the servers 12, 20 and between the servers 12, 20 themselves may be one and the same or may include a plurality of diverse networks. It will also be apparent to these skilled in the art that the described sequence of events, such as who requests the discovery of the geographic location may vary. For example, the devices 50 may request the geographic location of the nearby lighting units 42, 32 from the lighting management server 20 by sending the lighting management server 20 the sensed IDs. Alternatively, the caregivers/emergency responders 16, 18 may make the request in place of the emergency monitoring server 12. The request and any other discussed communication may be achieved using the shown technology including via the base station 44, the access point 34 and/or the network 24. Further variations of the present system would readily occur to a person of ordinary skill in the art and are encompassed by the following claims.

In another embodiment a sequence of the received lighting unit IDs of the lighting units 42, 32 and associated timestamps may be logged (e.g., periodically) in advance of an alarm condition, such as by the device 50, to track movement and the current location of the user. When the sequence is analyzed the trajectory/movement of the user may be determined, e.g., on the lighting management server 20 from the geographic locations associated with the IDs. Such stored history of the trajectory/movement of the user may also be used to assess the user's health condition and/or state of mind. For example, a detection of the user in a location and/or trajectory that is unusual for that user may be utilized for triggering further monitoring and/or for triggering an alarm.

In accordance with embodiments of the present system, the device 50 may configure the tracking parameters in accordance with the health condition of the associated user. The tracking parameters may include the triggering event/threshold, e.g., heart rate/ECG and respiratory rate, $SpO_2$, or their combination, to start tracking, and/or to adjust the frequency of detecting and reporting the lighting unit IDs. In other words, the devices 50 may trigger the reception and report of the lighting unit IDs and/or adjust the frequency/granularity according to the users health conditions. The users health conditions may be assessed either locally by the device 50 and/or may be returned by the emergency monitoring server 12. For example for a more acute user it may be desirable to achieve a higher accuracy of location tracking by more frequent detection and reporting of the lighting unit IDs. In another example, when a users condition deteriorates below a certain predefined level, the tracking process may be triggered for the user.

FIG. 2 illustrates a general tracking process 100 involving the lighting network, the devices and an emergency monitoring server in accordance with embodiments of the present system. The process first starts and thereafter, during act 102, the lighting management server 20 (e.g., FIG. 1) may store geographic locations of the lighting units 42, 32 in the database 22 together with corresponding lighting unit IDs. During act 104, the lighting units 42, 32 may transmit corresponding IDs locally (e.g., within the general vicinity of the corresponding lighting unit). During act 106, the body wearable devices 50 may detect the IDs of nearby lighting units 42, 32 and may detect a condition of the user. The body wearable devices 50 may thereafter transmit the detected lighting unit IDs to the emergency monitoring server 12 as well as information related to the detected condition. Then during act 108, the emergency monitoring server 12 may query and/or otherwise request the locations associated with the detected IDs of the lighting units 42, 32. During act 110, the lighting management server 20 may provide the emergency monitoring server 12 with the locations of the lighting units 42, 32 associated with the detected IDs. Thereafter, during act 112, the locations of the lighting units 42, 32 associated with the detected IDs may be provided to the caregivers/emergency responders 16, 18. As may be readily appreciated, information related to the user may be forwarded periodically or at other times and/or intervals to the emergency monitoring server 12 for example, for purposes of determining a condition of the user.

FIG. 3 shows a portion of a system 300 (e.g., emergency monitoring server, the lighting management server, the body wearable devices, etc.) in accordance with embodiments of the present system. The system 300 includes a processor 310 operationally coupled to a memory 320, a display 330, and input peripheral 370. In the case of a body wearable device, the system 300 may include one or more sensors 54. The sensors 54 may include a wireless receiver and/or electromagnetic radiation sensor, which receives and forwards corresponding sensor information, such as device IDs, user monitoring information such as alarm conditions, etc., to the processor 310. The memory 320 may be any type of non-transitory device for storing application data as well as other data related to the described operation. The application data and other data are received by the processor 310 for configuring (e.g., programming) the processor 310 to perform operation acts in accordance with the present system. The processor 310 so configured becomes a special purpose machine particularly suited for performing in accordance with the present system.

The user input portion 370 may include a keyboard, mouse, trackball or other device, including touch sensitive displays, which may be stand alone or be a part of a system, such as part of a personal computer, personal digital assistant (PDA), mobile phone, smart phone, set top box, television or other device for communicating with the processor 310 via any operable link. The input peripheral 370 may be operable for interacting with the processor 310 including enabling interaction within a user interface as described herein. Clearly the processor 310, the memory 320, display 330 and/or input peripheral 370 may all or partly be a portion of a computer system or other device such as a cellular station, lighting unit and/or other device (e.g., a cellular operator device, lighting operator device, etc.) as described herein.

The methods of the present system are particularly suited to be carried out by a computer software program, such program containing modules corresponding to one or more of the individual steps or acts described and/or envisioned by the present system. Such program may of course be embodied in a computer-readable medium, such as an integrated chip, a peripheral device or memory, such as the memory 320 or other memory coupled to the processor 310.

The program and/or program portions contained in the memory 320 configure the processor 310 to implement the methods, operational acts, and functions disclosed herein. The memories may be distributed, and the processor 310, where additional processors may be provided, may also be distributed or may be singular. The memories may be implemented as electrical, magnetic or optical memory, or any combination of these or other types of storage devices. Moreover, the term "memory" should be construed broadly enough to encompass any information able to be read from or written to an address in an addressable space accessible by the processor 310. With this definition, information accessible through a network 24 is still within the memory, for instance, because the processor 310 may retrieve the information from the network 24 for operation in accordance with the present system.

The processor 310 is operable for providing control signals and/or performing operations in response to input signals from the input peripheral 370, the sensors 54, as well as in response to other devices of a network 24 and executing instructions stored in the memory 320. The processor 310 may be an application-specific or general-use integrated circuit(s). Further, the processor 310 may be a dedicated processor for performing in accordance with the present system or may be a general-purpose processor wherein only one of many functions operates for performing in accordance with the present system. The processor 310 may operate utilizing a program portion, multiple program segments, and/or may be a hardware device utilizing a dedicated or multi-purpose integrated circuit.

Finally, the above discussion is intended to be merely illustrative of the present system and should not be construed as limiting the appended claims to any particular embodiment or group of embodiments. It should also be appreciated that numerous modifications and alternative embodiments may be devised by those having ordinary skill in the art without departing from the broader and intended spirit and scope of the present system as set forth in the claims that follow.

Accordingly, the specification and drawings are to be regarded in an illustrative manner and are not intended to limit the scope of the appended claims. In interpreting the appended claims, it should be understood that:

a) the word "comprising" does not exclude the presence of other elements or acts than those listed in a given claim;

b) the word "a" or "an" preceding an element does not exclude the presence of a plurality of such elements;

c) any reference signs in the claims do not limit their scope;

d) several "means" may be represented by the same item or hardware or software implemented structure or function;

e) any of the disclosed elements may be comprised of hardware portions (e.g., including discrete and integrated electronic circuitry), software portions (e.g., computer programming), and any combination thereof;

f) hardware portions may be comprised of one or both of analog and digital portions;

g) any of the disclosed devices, portions thereof, acts, etc., may be combined together or separated into further portions, acts, etc., unless specifically stated otherwise;

h) no specific sequence of acts or steps is intended to be required including an order of acts or steps indicated within a flow diagram; and i) the term "plurality of" an element includes two or more of the claimed element, and does not imply any particular range of number of elements; that is, a plurality of elements may be as few as two elements, and may include an immeasurable number of elements.

What is claimed is:

1. A method of obtaining a health condition and target location of a user associated with a body worn device including a sensor, the method comprising acts of:
    monitoring an indication of, using the sensor of body worn device, a health condition of user;
    determining, using the indication, whether a predetermined health condition is present in the user;
    maintaining a database, in a sewer, of information describing geographic locations of a plurality of lighting units, each lighting unit transmitting an identifier using modulated light;
    providing the body worn device with a lighting unit identifier sensor, the sensor receiving lighting unit identifiers of at least one of the plurality of lighting units;
    transmitting, by the body worn device, the received lighting unit identifiers with the indication in a message to the server via a network; and
    providing, by the server, a geographic location corresponding to the target location of the body worn device, using the database and the received lighting unit identifiers; and
    wherein said sensor and said lighting unit identifier sensor are a same camera for both receiving said lighting unit identifiers and sensing said a health condition of the user.

2. The method of claim 1, wherein the sensor is selected from being integrated with the body worn device and being flexibly placed on or around the body worn device to enhance detection performance.

3. The method of claim 2, wherein the sensor is wirelessly connected to the one or more body worn devices.

4. The method of claim 1, wherein the body worn device communicates at one of: when the alarm or alert is generated, periodically, at predetermined times, and when certain predetermined conditions are met.

5. The method of claim 4, wherein the communication further includes timestamps associated with one or more lighting unit identifiers for indicating the time a particular lighting unit identifier was received.

6. The method of claim 5, wherein the body worn device includes a memory for storing the lighting unit identifiers and associated timestamps indicating when each iteration of individual lighting unit identifier was received.

7. The method of claim 5, wherein the communicated one or more lighting unit identifiers include many lighting unit identifiers having different time stamps for obtaining a plurality of target locations and further comprising an act of forming a trajectory of the body worn device over time.

8. The method of claim 7, further comprising an act of using the trajectory to assess a health condition of the user of the body worn device.

9. The method of claim 1, wherein
    when a single lighting unit identifier is provided in the message, the location of the lighting unit is the target location, and
    when a plurality of lighting unit identifiers is provided in the message with temporally close timestamps the locations of the plurality of lighting units are used to determine the target location.

10. The method of claim 1, further comprising acts of:
    requesting the database to provide the one or more geographic locations of the lighting units; and alerting at least one emergency responder that a user wearing the body worn device requires assistance at the target location.

11. The method of claim 1, wherein the target location is identified with at least one of building section, floor number and room number; zip code, street name, and house number; a building or city map with target location identified; latitude, longitude and altitude; a relative position with respect to a predetermined location; and relative position with respect to another location conveyed in the query response.

12. A system for obtaining a health condition and geographic location of a user, the system comprising:
- a network formed of a plurality of lighting units and a database for maintaining information describing a geographic location of the plurality of lighting units, each lighting unit transmitting an identifier using modulated light;
- a server connected to the network for communicating an indication of the health condition of a user condition and a location of the user to a monitoring system; and
- a body worn device worn by a user and configured to detect the user health condition and communicate the indication of the user condition to the server, the body worn device having a camera to receive both the lighting unit identifiers of at least one of the plurality of lighting units and sense said health condition of the user, the server receiving lighting unit identifiers and the indication from the body worn device, determining if a predetermined health condition is present using the indication, determining a geographic location corresponding to the target location of the body worn device using the database and the received non-GPS identifiers.

13. The system of claim 12, wherein the target area is selected from selectable locations within buildings, hospitals, streets, and cities.

14. The system of claim 12, wherein the plurality of lighting units transmit the identifier using electromagnetic spectrum.

15. The system of claim 12, wherein the camera is selected from being integrated with the body worn device and being flexibly placed on or around the body worn device to enhance detection performance convenience and is connected to the body worn device by one of a wireless and hardwired attachment.

16. The system of claim 12, wherein the communication of the body worn device
- includes one or more timestamps associated with one or more lighting unit identifiers for indicating a time a particular lighting unit identifier was received, and
- is transmitted to the server at one of when the alarm or alert is generated, periodically, at predetermined times, and when certain predetermined conditions are met.

17. The system of claim 16, wherein the communicated one or more lighting unit identifiers include different time stamps indicating a trajectory of the body worn device over time, the trajectory indicating a health condition of the user wearing the body worn device.

18. The system of claim 12, wherein the target location is identified with at least one of a section in a building, floor number and room number; zip code, street name and house number, a building or city map with target location identified; latitude, longitude and altitude; a relative position with respect to a predetermined location; and relative position with respect to another location conveyed in the query response.

* * * * *